(12) United States Patent
Arai

(10) Patent No.: US 7,725,957 B2
(45) Date of Patent: Jun. 1, 2010

(54) TOUCH SENSITIZATION GLOVE

(75) Inventor: Yohich Arai, Saitama (JP)

(73) Assignee: Global Corporation, Hyogo (JP)

( * ) Notice: Subject to any disclaimer, the term of this patent is extended or adjusted under 35 U.S.C. 154(b) by 0 days.

(21) Appl. No.: 11/547,058

(22) PCT Filed: Apr. 2, 2004

(86) PCT No.: PCT/JP2004/004823

§ 371 (c)(1),
(2), (4) Date: Oct. 2, 2006

(87) PCT Pub. No.: WO2005/099608

PCT Pub. Date: Oct. 27, 2005

(65) Prior Publication Data

US 2007/0271676 A1 Nov. 29, 2007

(51) Int. Cl.
*A41D 19/00* (2006.01)
*A61B 5/103* (2006.01)
*A61B 5/117* (2006.01)
*A61F 5/24* (2006.01)

(52) U.S. Cl. ............... 2/161.7; 2/161.6; 2/159; 600/587; 128/95.1

(58) Field of Classification Search ............... 2/159, 2/161.7, 164, 904; 600/550, 587; 128/898, 128/878, 879; 401/7; 602/21; 132/312
See application file for complete search history.

(56) References Cited

U.S. PATENT DOCUMENTS

| 674,913 | A | * | 5/1901 | Fike ............... 401/7 |
|---|---|---|---|---|
| 2,092,318 | A | * | 9/1937 | Lindfelt ............... 2/161.2 |
| 2,694,396 | A | * | 11/1954 | Paschal ............... 601/138 |
| 3,821,817 | A | * | 7/1974 | Jorgensen ............... 2/169 |
| 4,657,021 | A | | 4/1987 | Perry et al. ............... 128/630 |
| 4,660,228 | A | | 4/1987 | Ogawa et al. |
| 4,793,354 | A | | 12/1988 | Wright et al. ............... 128/630 |
| 4,873,982 | A | | 10/1989 | Morrison ............... 128/630 |
| 5,704,670 | A | * | 1/1998 | Surplus ............... 294/25 |
| 5,876,745 | A | * | 3/1999 | Muraoka et al. ............... 424/448 |
| 5,946,727 | A | | 9/1999 | Wright et al. ............... 2/161.7 |
| 2002/0169389 | A1 | | 11/2002 | Morrison ............... 600/550 |

FOREIGN PATENT DOCUMENTS

| JP | 60193914 U | 12/1985 |
|---|---|---|
| JP | 61106146 A | 5/1986 |
| JP | 61289102 A | 12/1986 |
| JP | A-61-292182 | 12/1986 |
| JP | 02280731 A | 11/1990 |
| JP | B2-4-11872 | 3/1992 |
| JP | 05044248 U | 3/1995 |
| JP | 07013762 U | 7/1995 |
| JP | 07178149 A | 7/1995 |
| JP | 2002030506 A | 1/2002 |

* cited by examiner

*Primary Examiner*—Gary L Welch
*Assistant Examiner*—Amber R Anderson
(74) *Attorney, Agent, or Firm*—Porzio, Bromberg & Newman, P.C.

(57) ABSTRACT

A touch sensitization glove (1), comprising a sensitizing layer (2) and an external cover (3). The sensitizing layer (2) further comprises a first film (10) coming into contact with an object, a second film (12) superposed on the first film (10), and an air inlet (14) leading air between the first film (10) and the second film (12). The second film (12) is allowed to slidably move on the first film (10). Thus, lubricant can be eliminated, and an advanced touch sensitization glove can be provided.

10 Claims, 6 Drawing Sheets

TOUCH SENSITIZATION GLOVE

TECHNICAL FIELD

This invention relates to a glove for sensitizing the touch of a hand as for the hand-check (the palpation in the medical practice, for the confirmation of the state of surface finish in an industrial product and for others.

BACKGROUND ART

At the site of medical practice, for example, the hand-check that checks the condition of a body surface or a body interior of a patient by the touch of a hand is becoming popular. Exact judgment of the condition of the body of the patient with the hand results in early ascertainment of the cause of the disease. Further, the hand-check is significant also at the scene of self-health check because it can be put to practice by the patient oneself.

In the examination regarding breast cancer, for example, the practice of confirming the condition of the breast with the hand is generally adopted. Particularly in recent years, the early detection of breast cancer has become a very important task in view of the increase of the incidence rate of breast cancers. The breast cancer, when suffered to occur in the thoracic part, forms stiffness. When the stiffness is detected by the hand-check while it is still in a small size, the death rate of this disease can be decreased by early therapy.

Generally, a woman is enabled to confirm the presence or absence of this stiffness formed in her thoracic part by performing the hand-check with her hand across the thoracic part while her skin is wetted or covered with soap water as in the course of bathing. This method is aimed at enabling the condition of a body interior to be checked sensitively by decreasing the frictional resistance between the hand and the thoracic part. In the circumstance excepting the course of bathing, the frictional resistance that is generated between the hand and the thoracic part results in lowering the sensitivity of the hand and disabling exact detection of the stiffness.

A pad adapted to sensitize the touch of a hand irrespectively of the condition of a body skin and consequently allow early detection of stiffness possibly existing in the body interior has been known (JP-A SHO 61-292182). This pad is composed of a shell (bag) formed of a latex material or a natural rubber material and a lubricating liquid formed of silicone or glycol and retained in the shell. A woman client holds this pad between the thoracic part and the hand and moves the hand around. She is enabled to decrease the friction by the action of the lubricating liquid and check the thoracic part by oneself via the lubricating liquid and the shell of the latex material, for example.

The pad mentioned above, however, entails the problem that when the shell is broken by an external shock of some sort, the pad will become unusable because of leakage of the lubricating liquid from the interior and will suffer the leaking liquid to defile the environment as well. The pad requires the component materials thereof to be so selected that the shell may not suffer from seepage of the lubricating liquid. Therefore, when this selection is mistaken, the lubricating liquid will infiltrate the shell and gradually ooze out the shell.

Further, when this pad is used while the user remains in her standing position, the lubricating liquid in the interior thereof is inevitably gathered by the gravitational attraction in the lower part of the interior of the shell. The shortage of the lubricating liquid will occur throughout the upper part of the pad from the center thereof upward and the hand-check by oneself will be performed with difficulty.

Then, the combination of the lubricating liquid of silicone material and the shell of latex material are expensive in spite of the fact that they are characteristically difficult of mutual infiltration. Therefore, the pad has not been widely available in spite of an unusually high need for the pad. Further, the conventional pads are apt to be used repeatedly because their price range is expensive (several thousand yen, for example). When they are used in hospital, for example, they must be given a sterilizing treatment each time their use is repeated. They have consequently entailed problems in terms of convenience and hygiene.

This invention has been produced in view of the problems mentioned above and is aimed at providing a glove which can be manufactured very inexpensively and is capable of sensitizing the touch of a hand.

DISCLOSURE OF THE INVENTION

The touch sensitization glove contemplated by this invention is provided with a sensitizing layer allowed to contact an object and an external cover serving to fix a hand to the sensitizing layer and adapted to detect fine irregularities of the object by a hand inserted between the sensitizing layer and the external cover via the sensitizing layer, and characterized by the sensitizing layer having a first film allowed to contact the object, a second film superposed on the first film, and an air inlet adapted to introduce air between the first film and the second film and render the second film slidable on the first film.

The invention mentioned above is characterized by the fact that the air inlet is formed along the neighborhood of the peripheries of the first and second films.

Further, the invention mentioned above is characterized by the fact that the air inlet is formed on the first film side.

Then, the invention mentioned above is characterized by the fact that a basal sheet is attached in a separable state to the object side of the first film.

Further, the invention mentioned above is characterized by the fact that the user of the glove is prevented from inserting his hand into the air inlet by having the air inlet covered with the basal sheet.

Further, the invention mentioned above is characterized by the fact that the external cover has formed therein air holes for releasing the moisture of the hand.

Then, the invention mentioned above is characterized by the fact that the sensitizing layer and the external cover are formed of a transparent raw material.

Further, the invention mentioned above is characterized by the fact that the sensitizing layer and the external cover are formed in different colors for enabling visual confirmation of the position for the insertion of the hand.

Then, the invention mentioned above is characterized by the fact that the raw material for the first and second films is a synthetic resin.

The invention mentioned above is characterized by the fact that the raw material for the first and second films is an ethylene-vinyl acetate copolymer.

The invention mentioned above is characterized by the fact that the raw material for the first and second films is polyethylene.

The invention mentioned above is characterized by the fact that the raw material for the first and second films is Teflon (polytetrafluoroethylene).

The invention mentioned above is characterized by the fact that the raw material for the first and second films is an ethylene-vinyl alcohol copolymer.

The invention mentioned above is characterized by the fact that the first and second films have the durometer impact D hardness of not more than 36.

The invention mentioned above is characterized by the fact that the first and second films have a thickness of not more than 0.10 mm.

The invention mentioned above is characterized by the fact that the first and second films have an elongation percentage of not less than 700%.

The invention mentioned above is characterized by the fact that the air inlet formed in the sensitizing layer is set at a size allowing insertion of a hand and the insertion of a hand between the first and second films enables the glove to be utilized as a moisture-retaining glove.

BEST MODE OF EMBODYING THE INVENTION

The best mode of embodying this invention will be described in detail below by reference to the accompanying drawings.

Figure 1:
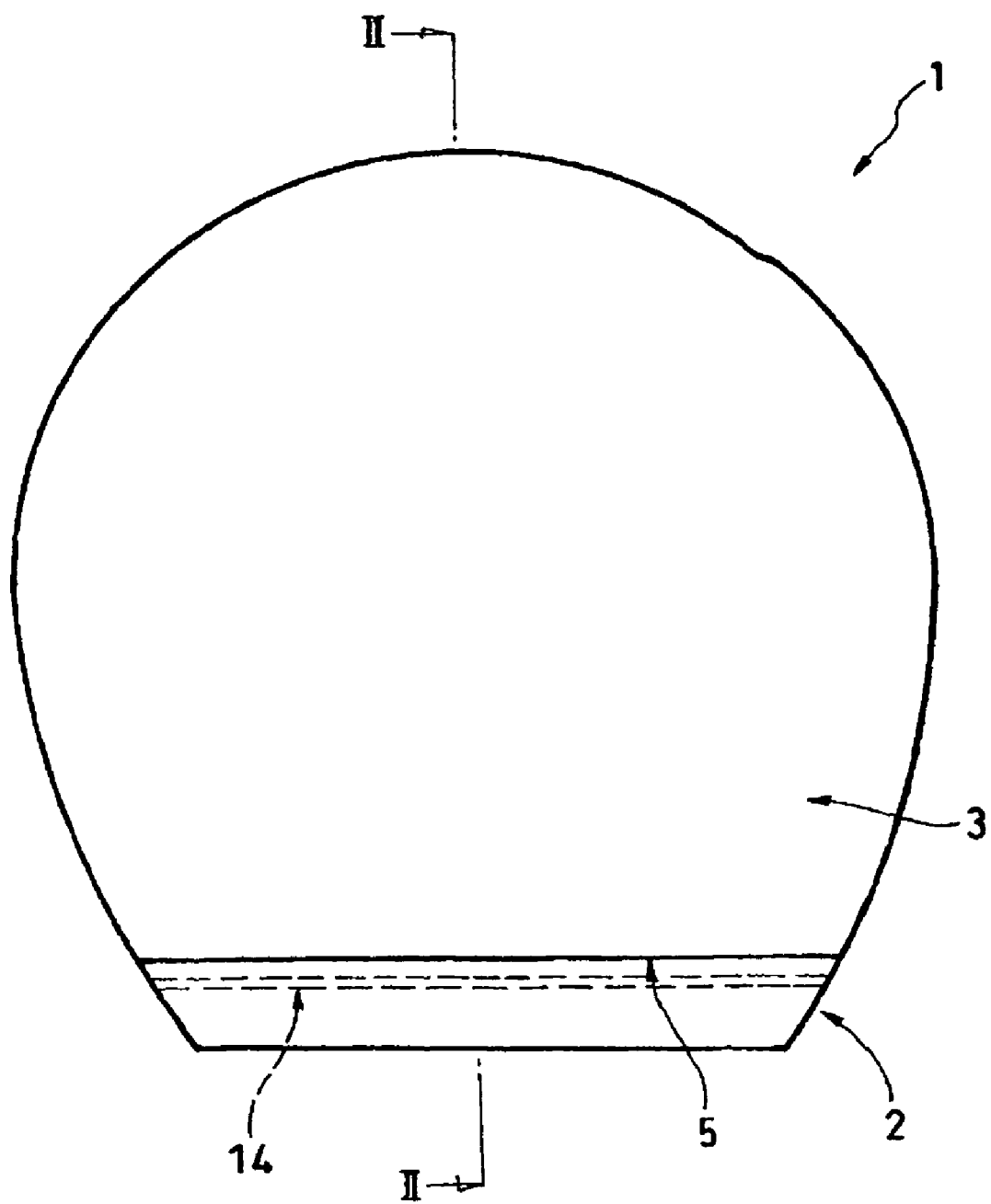
FIG. 1 is a plan view of a glove 1 according to the first mode of embodiment of this invention.
Figure 2:
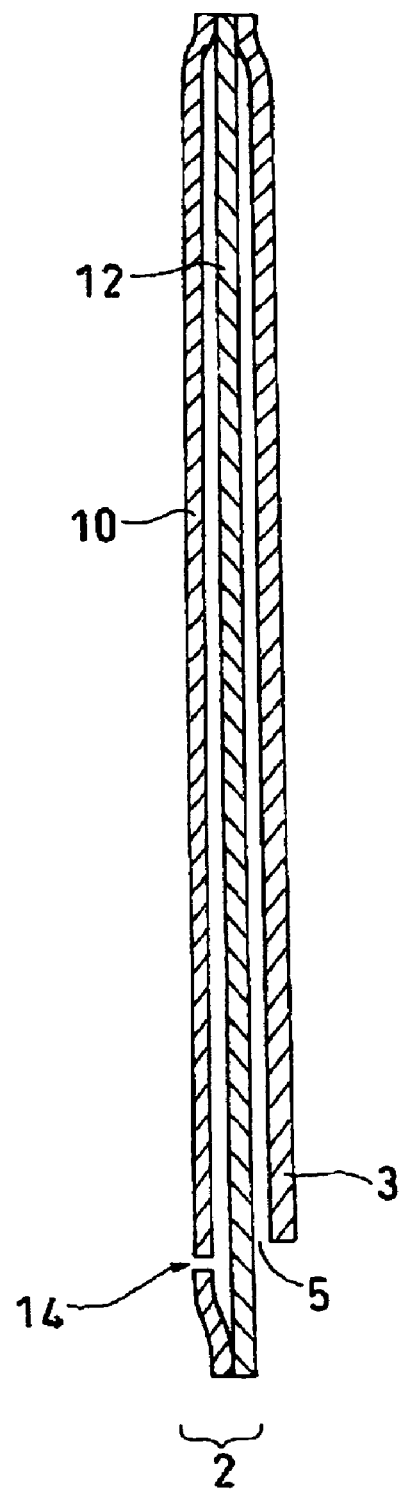
FIG. 2 is a cross section taken through FIG. 1 across the arrow line II-II.

In FIG. 1 and FIG. 2, a touch sensitization glove (hereinafter referred to as "glove") 1 according to the first mode of embodiment of this invention is illustrated. Incidentally, in the case of depicting the sectional structure of the glove 1 as in FIG. 2, the component members of the glove are shown in an exaggerated thickness with a view to rendering the drawing obvious.

The glove 1 is furnished with a sensitizing layer 2 allowed to contact an object and an external cover 3 serving to fix a hand to the sensitizing layer 2. Overall, the sensitizing layer 2 and the external cover 3 have a roughly elliptic shape. Part of the ellipse is linearly cut off so as to form an inserting opening 5 for allowing insertion of a hand. The sensitizing layer 2 and the external cover 3 are enabled, by having the peripheries thereof adhere mutually, to assume the shape of a bag and allow a hand to be inserted between the sensitizing layer 2 and the external cover 3 via the inserting opening 5. The external cover 3, though not particularly illustrated herein, has formed therein a plurality of air holes serving to release the moisture of the hand. Thus, it assumes the so-called meshed shape and ensures prolonged comfortable use. Though the glove 1 is illustrated in the elliptic shape herein, it may be formed in the shape of a glove that enables the individual fingers to be inserted independently of each other. Further, it may be formed in such a shape that the index finger up to the little finger are jointly inserted into one inseparable part and the thumb is inserted into an independent part.

The sensitizing layer 2 is furnished with a first film 10 allowed to touch an object and a second film 12 superposed on the first film 10. This sensitizing layer 2 also has an air inlet 14 formed therein and utilizes it for introducing air between the first film 10 and the second film 12 and preventing them from mutually adhering. Consequently, the second film 12 is enabled to move smoothly relative to the first film 10. Specifically, the air inlet 14 is formed in the shape of a slit along the neighborhood of an edge of the first film 10. Since the air inlet 14 is formed on the side of the first film 10, this air inlet 14 is enabled to open toward the object.

Figure 3:
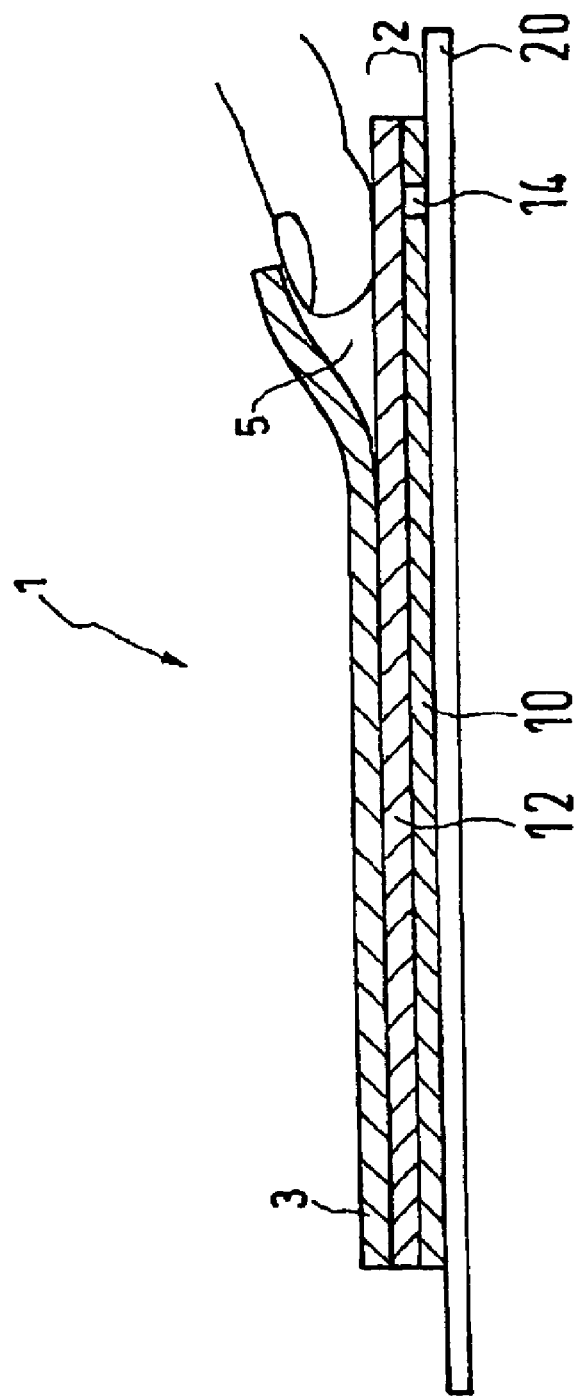
FIG. 3 is a cross section illustrating the packaging state of the glove 1.

In FIG. 3, the glove 1 is illustrated in the state of a package that is offered as a commodity to the user. A basal sheet 20 made of paper is tacked to the first film 10's side of the glove 1 and can be easily peeled off. The basal sheet 20 keeps the air inlet 14 covered till use, therefore the basal sheet is enabled to prevent the user from inadvertently inserting his hand into the air inlet 14. Then dirt, dust, and the like can't enter the sensitizing layer 2 via the air inlet 14 as well. When the basal sheet 20 is peeled off after the insertion of his hand via the inserting opening 5, the air inlet 14 is actually opened to introduce air between the first and second films 10, 12 and ready the glove 1 for use. The material for the basal sheet 20 does not need to be limited to paper. Film or other material may be optionally used instead.

For the sensitizing layer 2 and the external cover 3, transparent materials are used. In the present mode of embodiment, a colorless and transparent material is used for the sensitizing layer 2 (the first and second films 10, 12) and a pink transparent material is used for the external cover 3. By thus giving the sensitizing layer 2 and the external cover 3 mutually different colors (including a transparent color), the user is enabled to discover visually the inserting opening 5 that allows insertion of his hand. Though the case of coloring the raw materials themselves is illustrated herein, this invention naturally does not need to adhere exclusively to this method but may accomplish distinction of the inserting opening 5 by partially printing the relevant films.

The first and second films 10 and 12 use a synthetic resin material, specifically an ethylene-vinyl acetate copolymer (EVA) film having a thickness of 0.10 mm. The thickness of the film is preferably not more than 0.10 mm and more preferably not more than 0.03 mm. The ethylene-vinyl acetate copolymer enables each of two films made thereof to slide on the other smoothly and manifests softness suitable for sensitizing the touch. Unlike the chlorine-based raw material, this copolymer material is endowed with the merit of scarcely emitting a harmful substance during the course of waste disposal.

Besides the synthetic resin material mentioned above, the synthetic resin materials that are usable herein include polyolefin-based materials such as polyethylene (PE) and polypropylene (PP), polyester-based materials such as polystyrene (PS), polyethylene terephthalate (PET), and polyethylene isophthalate (PEI), and homopolymers or copolymers such as nylon (NY), polyvinyl chloride (PVC), ethylenevinyl alcohol copolymer (EVOH), polyvinyl alcohol (PVA), and polyvinylidene chloride (PVDC), for example. Among other synthetic resin materials enumerated above, polyethylene and ethylene-vinyl alcohol prove to be particularly advantageous. For the first and second films 10 and 12, a film manufactured by using these synthetic resins either alone or in the form of a mixture may be used. For the first and second films 10 and 12, a laminated film manufactured by using these synthetic resins may be used. Further, the synthetic resin film may have the surface thereof coated with a coating agent known to the public for the purpose of imparting a good sliding property and an antistatic property to the film. Incidentally, the first and second films 10 and 12 have the durometer impact D hardness thereof set at not more than 36 (SHORE D). Therefore the first and second films 10 and 12 may be flexed easily and be slidable on each other since the rigidity of the raw material is decreased. Incidentally, this durometer impact D hardness (SHORE D hardness) is defined as in ISO 7619 and ISO 868 and indicates a numerical value to be measured by depressing a measuring needle into a given material. The first and second films 10 and 12 preferably have the elongation percentage thereof set at not less than 700% in order that the films, while the glove is being used for hand-check, may be elongated and enabled to follow the elongation of the skin. When the thickness of the film is set up in 0.03 mm, the first and second films 10 and 12 preferably have the breaking strength of not less than 2.7 N. Though the external cover 3 in the present embodiment uses perfectly the same raw material as the first and second films 10 and 12, these component parts may optionally use mutually different raw materials.

Figure 4:
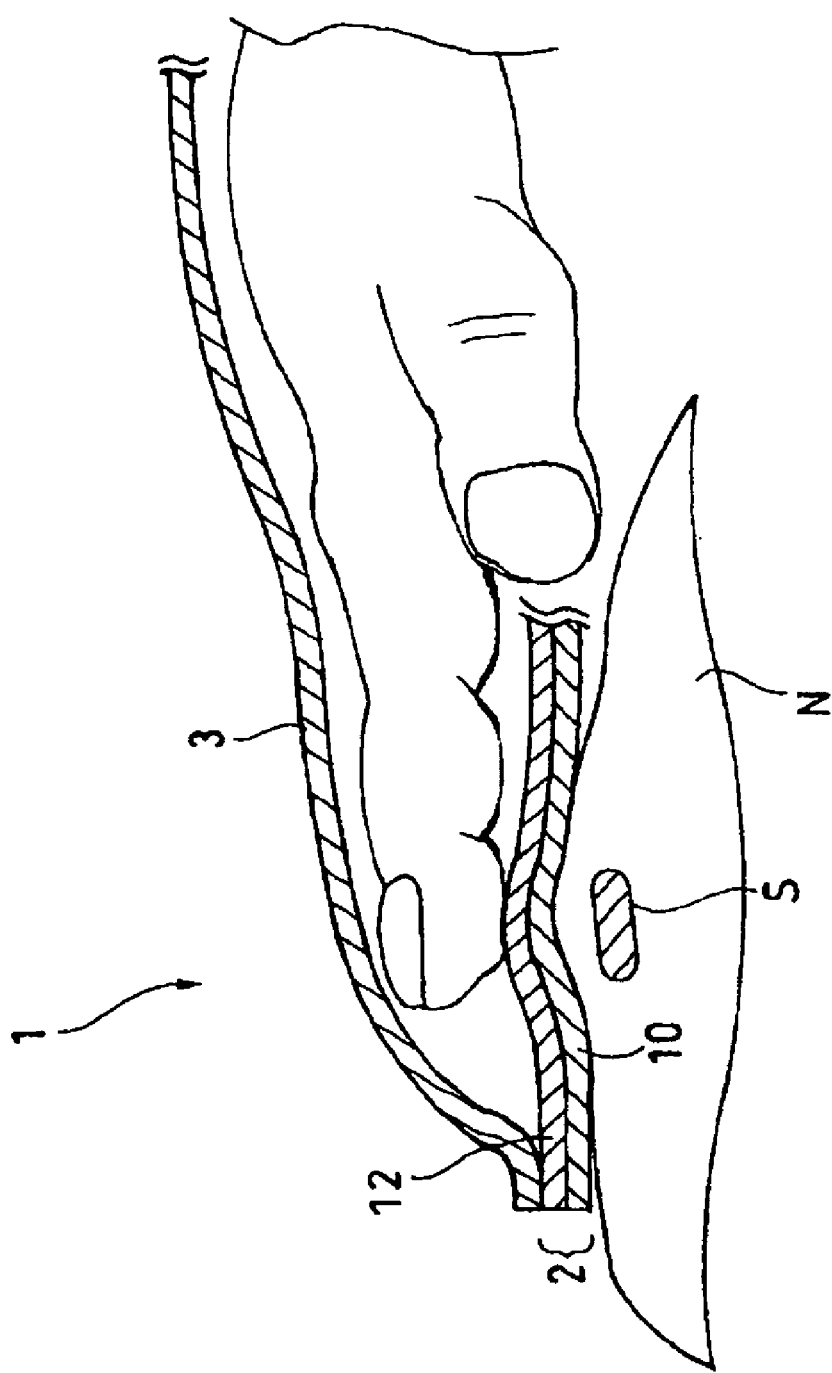
FIG. 4 is a cross section illustrating the state in which a user's hand is inserted in the glove 1.
Figure 5:
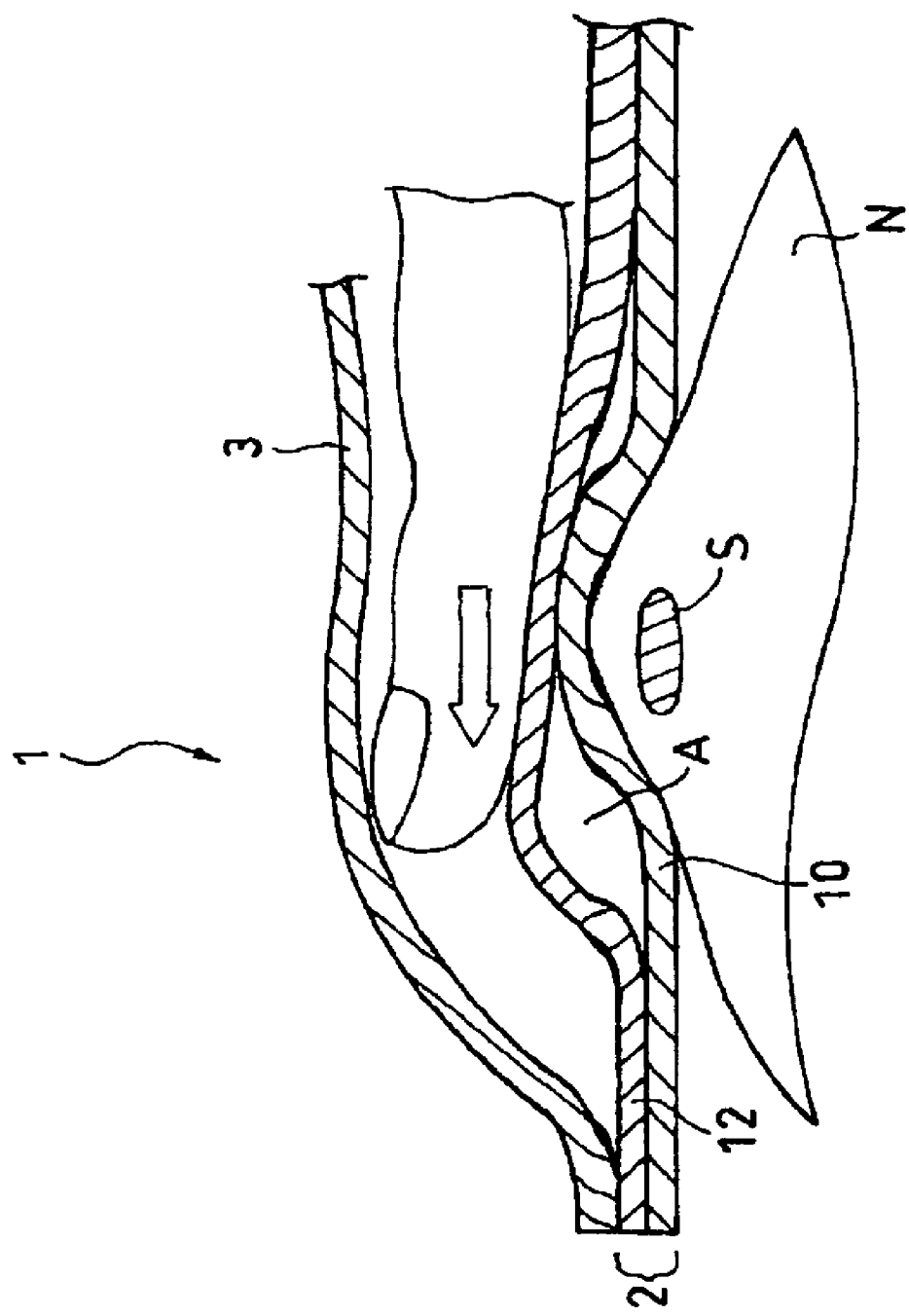
FIG. 5 is a principle diagram illustrating the state in which the glove 1 is being used for checking an object with a hand.
Figure 6:
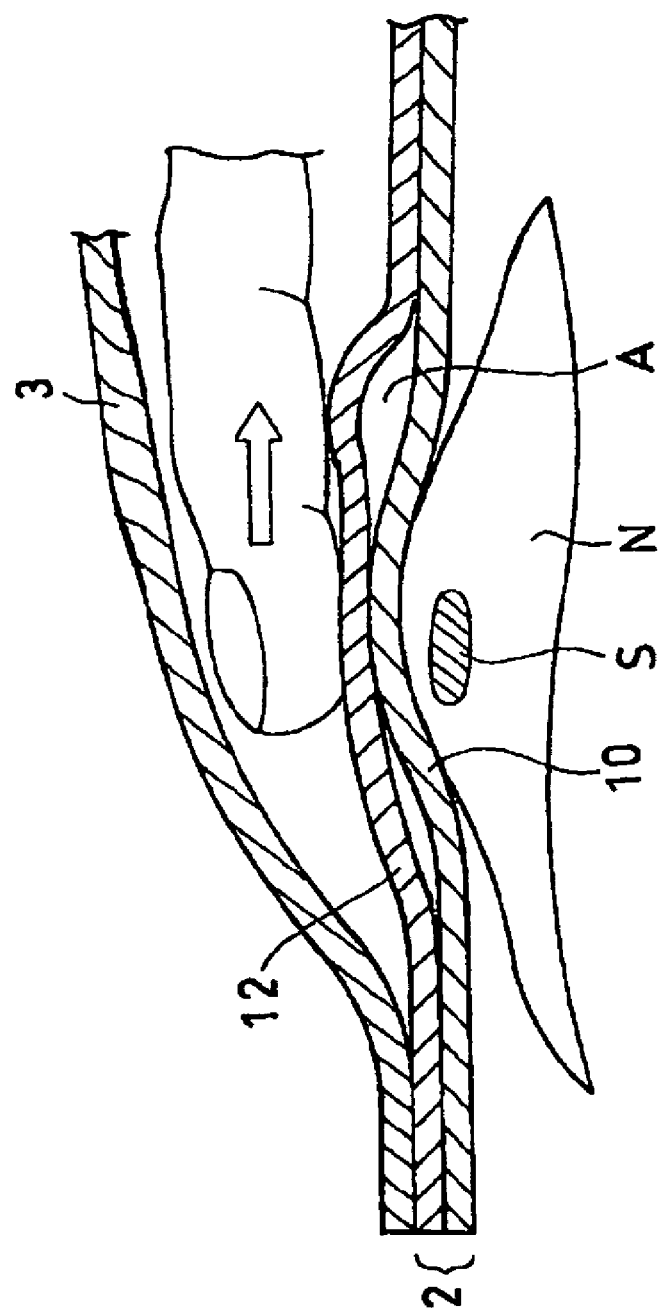
FIG. 6 is a principle diagram illustrating the state in which the glove 1 is being used for checking an object with a hand.

FIG. 4~FIG. 6 illustrate in type section the state in which the glove 1 is used for medical examination in search of breast cancer. As illustrated in FIG. 4, the hand is inserted between the sensitizing layer 2 and the external cover 3 and made to bring the sensitizing layer 2 into contact with the breast N of the thoracic part. For example, the sensitizing layer 2 is pressed down on the breast N and the cushions of the first joints of the three fingers (index finger, middle finger, and third finger) are made to touch the breast N while they are kept moving along the path of a circle about 5~7 cm in diameter. Specifically, first the breast N is examined with light pressure, then it is examined with slightly strong pressure, and this cycle is performed up to several repetitions, and the bulging region of the breast N is checked in detail.

When the hand-check is performed by moving the hand along the path of a circle about 5~7 cm in diameter, the finger tips are moved while the second film 10 is kept sliding on the first film 10 as illustrated in FIG. 5 and FIG. 6. As a result, the first film 10 adheres closely to the skin and it is integrated with the skin, although the second film 12 adheres closely to the user's hand and it is integrated with the tips of the fingers. Since the air A is introduced between the first film 10 and the second film 12 via the air inlet 14, the air A prevents the first film 10 and the second film 12 from adhering closely to each other by negative pressure. As a result, the sliding resistance is decreased and the fine irregularities on the surface of the breast N and the stiffness S existing in the interior thereof can be sensitively discovered.

Since the glove 1 according to the present mode of embodiment enables the first and second films 10 and 12 to be directly slid on each other without a lubricating liquid in the interior thereof, it causes no anxiety about leakage of liquid. And furthermore, the size and weight of the glove 1 is decreased. In the mode of the present embodiment, for example, when the glove 1 in the state of being pasted to the basal sheet 20 (FIG. 3) is folded into a small size, it can be distributed in the market in the form of a package measuring about 5 cm square and about 2 mm in thickness and weighing not more than 10 g. Since the conventional glove contains a lubricating liquid in a large volume, the distribution in this form has never been achieved.

Further, since the basal sheet 20 keeps the air inlet 14 tightly shut till use, consequently the basal sheet 20 prevents the user from inserting his hand inadvertently therein, and keeps dirt and the like out of the sensitizing layer 2 and makes the operation of the glove 1 easy for the hand-check. As a result it is made possible to obtain the glove 1 which, as manufactured goods, enjoys great convenience of use throughout from the step of distribution to the step of actual use. In the empty space between the sensitizing layer 2 and the external cover 3, for example, a paper containing the instruction written as with arrow marks regarding the method of inserting a hand may be placed with a view to positively showing the position for the insertion of the hand. In this case, the paper containing the instruction is supposed to be removed when the glove is put to use.

Further in the present mode of embodiment, since the cost of production can be greatly decreased, the glove 1 may be used as disposable goods. As a result, the medical practitioners daily examining numerous patients in search of symptoms of breast cancer are allowed to change the gloves 1 on each occasion of examination and consequently enabled to maintain themselves and the patients in a highly hygienic state as compared with the practitioners having their hands directly touch the skins or the physicians using a common glove repeatedly.

Since this glove 1 uses a low-pollution polymer material, the glove 1 prevents an environmental pollution when it is used as disposable goods as mentioned above. Particularly, the ethylene-vinyl acetate copolymer is unusually favorable in terms of both function and price and is enabled to sensitize the touch.

Though the case of forming the sensitizing layer 2 with two films 10 and 12 is illustrated in the present mode of embodiment, this invention does not need to adhere to this case but may use three or more films for the sensitizing layer 2. Though the case of introducing air between the two films and enabling these films to move smoothly relative to each other without using a lubricating liquid is also illustrated herein, it is permissible to lower the frictional resistance further by inserting talcum powder, for example, between the first and second films 10 and 12.

While the air inlet 14 has been illustrated as limited to the case of forming it in the shape of a slit, this invention does not need to adhere to this case but may allow it to be formed in other shape. It is permissible to form a plurality of small air inlets instead, which are capable of preventing the user from inserting his hand inadvertently between the first and second films 10 and 12. Meanwhile, by having the air inlet 14 set in advance at a size allowing insertion of a hand, the glove 1 which has been used for the hand-check may be used like an ordinary PVC glove that is resistant to water. The used glove may be utilized as a moisture-retaining glove when it is caused to cover a hand that has been coated in advance with hand cream, for example.

Incidentally, though the method for utilization that is aimed mainly at medical treatments such as the medical examination in search of breast cancer has been illustrated in the preceding mode of embodiment, this invention does not need to be limited thereto but may be utilized at all scenes that necessitate the touch to be sensitized. For example, this invention is available for other uses as in the case of finally checking the state of surface finish of a product of manufacturing industry or in the case of confirming the surface irregularities of a product of art.

The entire disclosure of International Patent Application No. PCT/JP2004/004823 filed on Apr. 2, 2004 including specification, claims, drawings, and summary are incorporated herein by reference in its entirety.

INDUSTRIAL APPLICABILITY

This invention enables production of a touch sensitization glove light and compact and free from anxiety about leakage of a lubricating liquid. Further, since the invention permits great decrease in the cost of production, the product can be utilized as a disposable article.

What is claimed is:

1. A touch sensitization glove comprising a sensitizing layer allowed to contact an object and an external cover serving to fix a hand to the sensitizing layer to detect fine irregularities of the object by a hand inserted between the sensitizing layer and the external cover via the sensitizing layer, and characterized by the sensitizing layer comprising a first film allowed to contact the object, a second film superposed on the first film, and an air inlet being formed in said first film as a slit or a plurality of air inlets along the neighborhood of the peripheries of the first and second films for introducing air between the first film and the second film during use to prevent them from mutually adhering and render the second film slidable on the first film without lubricating liquid in the interior thereof, a basal sheet is attached in a peelable state to the object side of the first film, wherein an entire surface of the glove is covered with the basal sheet, wherein a surface area of the basal sheet is larger than the area of the entire surface of the glove, wherein the raw material for the first and second films is a flat resin to allow the first and second films to slide on each other smoothly and never to retain an alien substance, and to detect fine irregularities of the object and the sensitizing layer and the external cover are formed of a transparent raw material through which the object is checked, wherein the first and second films have the durometer impact D hardness of not more than 36, wherein the first and second films have a thickness of not more than 0.10 mm.

2. The touch sensitization glove according to claim 1, wherein the user of the glove is prevented from inserting his hand into the air inlet by having the air inlet covered with the basal sheet.

3. The touch sensitization glove according to claim 1, wherein the external cover has formed therein air holes for releasing the moisture of the hand.

4. The touch sensitization glove according to claim 1, wherein the sensitizing layer and the external cover are formed in different colors for enabling visual confirmation of the position for the insertion of the hand.

5. The touch sensitization glove according to claim 1, wherein the raw material for the first and second films is an ethylene-vinyl acetate copolymer.

6. The touch sensitization glove according to claim 1, wherein the raw material for the first and second films is polyethylene.

7. The touch sensitization glove according to claim 1, wherein the raw material for the first and second films is Teflon (polytetrafluoroethylene).

8. The touch sensitization glove according to claim 1, wherein the raw material for the first and second films is an ethylene-vinyl alcohol copolymer.

9. The touch sensitization glove according to claim 1, wherein the first and second films have an elongation percentage of not less than 700%.

10. The touch sensitization glove according to claim 1, wherein the air inlet formed in the sensitizing layer is set at a size allowing insertion of a hand and the insertion of a hand between the first and second films enables the glove to be utilized as a moisture-retaining glove.

* * * * *